(12) United States Patent
Deshpande et al.

(10) Patent No.: US 11,624,719 B2
(45) Date of Patent: Apr. 11, 2023

(54) SYSTEM AND METHOD FOR REAL-TIME NON-INVASIVE ESTIMATION OF FOOD QUALITY WITHIN ENCLOSED PACKAGE

(71) Applicant: Tata Consultancy Services Limited, Mumbai (IN)

(72) Inventors: Parijat Deshpande, Pune (IN); Jayita Dutta, Pune (IN); Beena Rai, Pune (IN)

(73) Assignee: TATA CONSULTANCY SERVICES LIMITED, Mumbai (IN)

(*) Notice: Subject to any disclaimer, the term of this patent is extended or adjusted under 35 U.S.C. 154(b) by 0 days.

(21) Appl. No.: 17/451,451

(22) Filed: Oct. 19, 2021

(65) Prior Publication Data
US 2022/0120703 A1 Apr. 21, 2022

(30) Foreign Application Priority Data
Oct. 20, 2020 (IN) .............................. 202021045759

(51) Int. Cl.
*G01N 27/02* (2006.01)
*G01N 33/14* (2006.01)

(52) U.S. Cl.
CPC .......... *G01N 27/026* (2013.01); *G01N 33/14* (2013.01)

(58) Field of Classification Search
CPC .. G01N 33/02; G01N 33/5438; G01N 1/2226; G01N 27/4141; G01N 27/026; G01N 33/14
See application file for complete search history.

(56) References Cited

U.S. PATENT DOCUMENTS 9,201,068 B2 * 12/2015 Suni ................... G01N 33/5438
2003/0155346 A1 * 8/2003 Simic-Glavaski .... A47J 45/061
219/438

(Continued)

OTHER PUBLICATIONS

Interdigitated array microelectrode based impedance biosensor coupled with magnetic nanoparticle-antibody conjugates for detection of *Escherichia coli* O157:H7 in food samples, Apr. 2006 (Year: 2006).*

(Continued)

*Primary Examiner* — Alesa Allgood
(74) *Attorney, Agent, or Firm* — Finnegan, Henderson, Farabow, Garrett & Dunner, LLP

(57) ABSTRACT

This disclosure relates generally to a system and method for real-time non-invasive estimation of food quality within enclosed package. Existing works utilize invasive methods that require direct contact of the food item with the sensors. In the present disclosure, a potential is applied over a plurality of frequencies through the food item contained the enclosed package which includes a plurality of polyethylene layers and a conducting layer arranged between two adjacent polyethylene layers using electrochemical impedance spectroscopy. Values of electrical voltages and the electrical impedances of the food item are then obtained. A plurality of features is derived from the obtained values of the electrical voltages and the electrical impedances using a trained model. The present disclosure estimates the quality of the food item in real-time by co-relating the plurality of derived features with the quality of the food item contained inside the enclosed package.

9 Claims, 12 Drawing Sheets

(56) References Cited

U.S. PATENT DOCUMENTS

2014/0011286 A1* 1/2014 Potyrailo .......... G01N 33/0031
427/466
2018/0252674 A1* 9/2018 Hansen ................ G01N 27/286

OTHER PUBLICATIONS

Zhao, Xin et al., "Electrical Impedance Spectroscopy for Quality Assessment of Meat and Fish: A Review on Basic Principles, Measurement Methods, and Recent Advances", Journal of Food Quality, July 2017, vol. 2017, Hindawi, https://downloads.hindawi.com/journals/jfq/2017/6370739.pdf.

Mustafa, Fatima et al., "Chemical and Biological Sensors for Food-Quality Monitoring and Smart Packaging", Foods, Oct. 2018, vol. 7 (10), NCBI, https://www.mdpi.com/2304-8158/7/10/168.

Mustafa, Fatima et al., "Nanotechnology-based approaches for food sensing and packaging applications", RSC Advances, Apr. 2020, vol. 10 (33), RSC, https://pubs.rsc.org/en/content/articlepdf/2020/ra/d0ra01084q.

Zavadlav[1], Sandra et al., "Utilitzing Impedance for Quality Assessment of European Squid (*Loligo vulgaris*) during Chilled Storage", Foods, Oct. 2019, Publisher: NCBI, https://www.mdpi.com/2304-8158/8/12/624.

Mishra[1], Geetesh Kumar et al., "Food Safety Analysis Using Electrochemical Biosensors", Foods Sep. 2018, vol. 7 (9), NCBI, https://www.mdpi.com/2304-8158/7/9/141.

Anukiruthika, T. et al., "Multilayer packaging: Advances in preparation techniques and emerging food applications", Foods, Apr. 2020, vol. 19 (3), PubMed, https://onlinelibrary.wiley.com/doi/epdf/10.1111/1541-4337.12556.

* cited by examiner

1. Polyethylene
2. Polyethylene
3. Aluminum foil
4. Polyethylene
5. Paper board
6. Polyethylene

100

US 11,624,719 B2

SYSTEM AND METHOD FOR REAL-TIME NON-INVASIVE ESTIMATION OF FOOD QUALITY WITHIN ENCLOSED PACKAGE

PRIORITY CLAIM

This U.S. patent application claims priority under 35 U.S.C. § 119 to: India Application No. 202021045759, filed on Oct. 20, 2020. The entire contents of the aforementioned application are incorporated herein by reference.

TECHNICAL FIELD

This disclosure relates generally to food quality estimation, and more particularly to system and method for real-time non-invasive estimation of food quality within enclosed package.

BACKGROUND

Global food wastage is indeed a big challenge today. According to Food and Agriculture Organization (FAO)—United Nations, food wastage accounts to 1.3 billion tons annually. The wastage is found at every node of food supply chain starting from farms to consumers and is largely affected by the variation of environmental parameters over time. This wastage has a considerable negative impact on the society, environment, and world economy. One in every 9 persons in the world starves and there is an economic loss of 1.2 trillion USD.

Main reason behind said food wastage is inability to monitor the variation of food quality in real-time under different supply chain scenarios. To address this challenge real time monitoring and prediction of food quality for variety of foods becomes essential. This would enable dynamic decisions on rerouting, repurposing, and recycling.

SUMMARY

Embodiments of the present disclosure present technological improvements as solutions to one or more of the above-mentioned technical problems recognized by the inventors in conventional systems. For example, in one embodiment, a method for real-time non-invasive estimation of food quality within enclosed package is provided. The method includes applying, via one or more hardware processors, a potential over a plurality of frequencies through a food item contained inside an enclosed package using electrochemical impedance spectroscopy; obtaining, via the one or more hardware processors, values of electrical voltages and electrical impedances of the food item as a function of frequency of the applied potential; deriving, using a trained model via the one or more hardware processors, a plurality of features from the values of the electrical voltages and the electrical impedances obtained, wherein the trained model is trained on an impedance spectrum and a voltage spectrum data obtained by varying the frequency over a range of voltages to characterize the food item and correlate with quality; and estimating, via the one or more hardware processors, the quality of the food item in real-time by co-relating the plurality of derived features with the quality of the food item contained inside the enclosed package.

In another aspect, there is provided a system for assessing insider influence on enterprise assets is provided. The system comprises: a memory storing instructions; one or more communication interfaces; and one or more hardware processors coupled to the memory via the one or more communication interfaces, wherein the one or more hardware processors are configured by the instructions to: apply, a potential over a plurality of frequencies through a food item contained inside an enclosed package using electrochemical impedance spectroscopy. The system further comprises obtaining values of electrical voltages and electrical impedances of the food item as a function of frequency of the applied potential; derive, using a trained model, a plurality of features from the values of the electrical voltages and the electrical impedances obtained, wherein the trained model is trained on an impedance spectrum and a voltage spectrum data obtained by varying the frequency over a range of voltages to characterize the food item and correlate with quality; and estimate, the quality of the food item in real-time by correlating the plurality of derived features with the quality of the food item contained inside the enclosed package.

In yet another aspect, there are provided one or more non-transitory machine-readable information storage mediums comprising one or more instructions which when executed by one or more hardware processors cause applying, via one or more hardware processors, a potential over a plurality of frequencies through a food item contained inside an enclosed package using electrochemical impedance spectroscopy; obtaining, via the one or more hardware processors, values of electrical voltages and electrical impedances of the food item as a function of frequency of the applied potential; deriving, using a trained model via the one or more hardware processors, a plurality of features from the values of the electrical voltages and the electrical impedances obtained, wherein the trained model is trained on an impedance spectrum and a voltage spectrum data obtained by varying the frequency over a range of voltages to characterize the food item and correlate with quality; and estimating, via the one or more hardware processors, the quality of the food item in real-time by co-relating the plurality of derived features with the quality of the food item contained inside the enclosed package.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Figure 1:
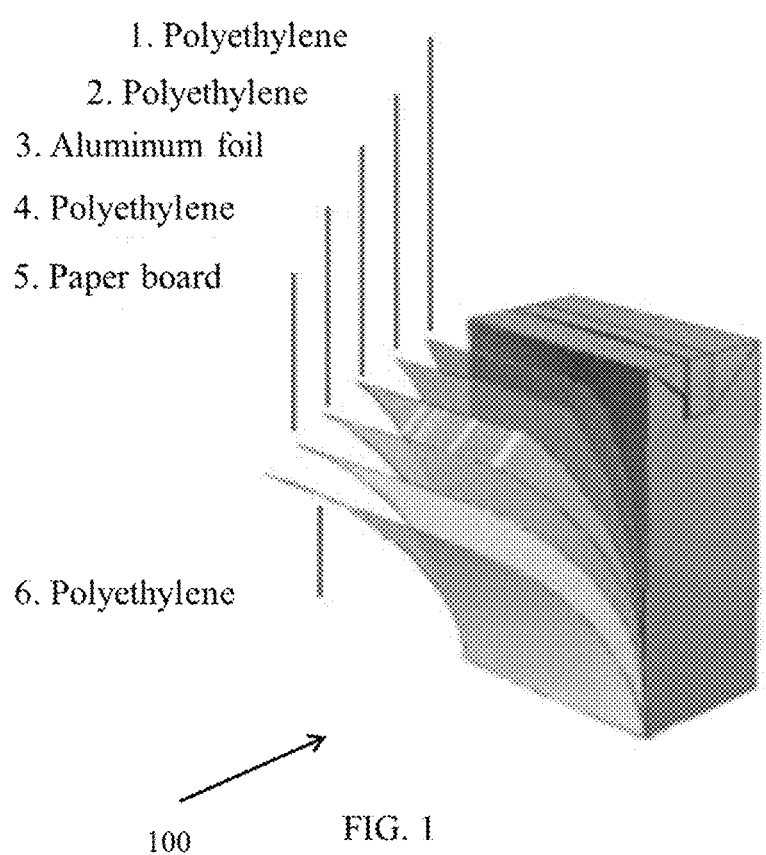
FIG. 1 illustrates an example of an enclosed package in accordance with an example embodiment of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following claims.

Currently various conventional methods for monitoring quality of food items are available. For instance, various chemical and biological sensors for food monitoring are available that sense various attributes of the packaged food to measure, for example, freshness markers, allergens, pathogens, adulterants, and toxicants via invasive means. However, most sensors are still in the development stage and need significant work before implementation in real-world applications. Issues like sensitivity, selectivity, robustness, and safety of the sensing materials due to potential contact or migration in food need to be established. Various other known techniques for monitoring quality of food such as fish, meat, etc. utilize invasive methods that require direct contact of the food item with the sensors. However, in certain scenarios it is not desirable to expose the food item to the sensors, for example, when the food item is packaged in a sealed container or an enclosed package. An example of such food item may be ready-to-consume-beverages packaged in a container.

Various embodiments disclosed herein provides method and system for estimating quality of food item packaged in an enclosed package. The enclosed package may include a plurality of polyethylene layers and a conducting layer arranged between two adjacent polyethylene layers. When the food item contained in the enclosed package is in contact with the enclosed package packaging layers, the disclosed system may determine the quality of food item by using Electrochemical Impedance Spectroscopy (EIS).

An important contribution of the disclosed embodiments is that the conducting layer is configured as special functionalized micro-electrodes for specific quality indicators associated with the respective food item contained in the enclosed package. In an embodiment, the quality indicators may include, but are not limited to pH change, growth of bacterium such as Alicyclobacillus Bacteria, and so on. When the food comes in contact with the micro electrodes (gold-plated) etched on the Aluminium layer of the packaging material, the functionalized micro-electrodes created between the conducting material and the respective food item determines a value of electrical voltage and impedance of the beverage as a function of frequency of an applied potential. Herein, it will be understood that the polyethylene layers may include micro-openings that will expose the food item within the enclosed package to the electrodes etched onto the Aluminium layer. The value of the electrical voltage and impedance may be input to a trained model trained predicting the quality of the beverage based on the value of the electrical voltage and impedance. In an embodiment, the trained model may be trained on an impedance spectrum and a voltage spectrum data obtained by sweeping the frequency over a range of AC (alternating current) to characterize the fluid and correlate with quality.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following embodiments described herein.

Referring now to the drawings, and more particularly to FIG. 1 through 7, where similar reference characters denote corresponding features consistently throughout the figures, there are shown preferred embodiments and these embodiments are described in the context of the following exemplary system and/or method.

FIG. 1 illustrates an example of an enclosed package 100 in accordance with an example embodiment of the present disclosure. For the brevity of description, the enclosed package 100 is shown to assume a cuboid shape, however it will be understood that the enclosed package 100 may assume any shape other than the shape and size shown.

The enclosed package 100 may be configured from a plurality of layers. As illustrated in FIG. 1, the plurality of layers may include a plurality of ethylene layers (for example, layers 1, 2, 4 and 5) and a conducting layer (for example, a layer 3). The polyethylene layers may serve various purposed for example. The purpose of polymer/polyethylene layers is to ensure non-reaction with food in contact with the inner walls of the package. In an embodiment, the conducting layer may be Aluminium layer. Typically, the Aluminium layer is a protective layer that prevents oxidation due to light that may cause damage to food item inside the enclosed package.

In an embodiment, the conducting layer may be configured as functionalized micro-electrodes corresponding to the food item contained in the enclosed package. Herein, the term 'functionalized micro-electrodes' refers to the property of the conducting layer modified to act like functionalized micro-electrode array by virtue of etching electrode configuration thereon. Herein, the functionalized micro-electrode array may be fabricated by using thin-film technologies. The quality of every food item may be determined based on a specific parameter/indicator. For example, if the food item contained in the enclosed package is orange juice, then in one example scenario, the quality indicator may be pH of the orange juice. Herein, the 'functionalized' micro-electrodes refer to a distinct configuration of Aluminium layer corresponding to orange juice that may facilitate in determination of the value of the indicator specific to the orange juice, for example, the value of pH of orange juice may be determined upon coming in contact with the micro electrodes etched on the Aluminium layer of the packaging material. In an embodiment, the micro-electrodes may be coated with a polymer which may attract only the indicator of interest (which is to be measured) for determining food quality.

In an embodiment, a method and a system may be utilized for estimating the quality of food item contained in the enclosed package, for example the enclosed package 100. The method and system are explained further with reference to FIGS. 2 and 3 below.

Figure 2:
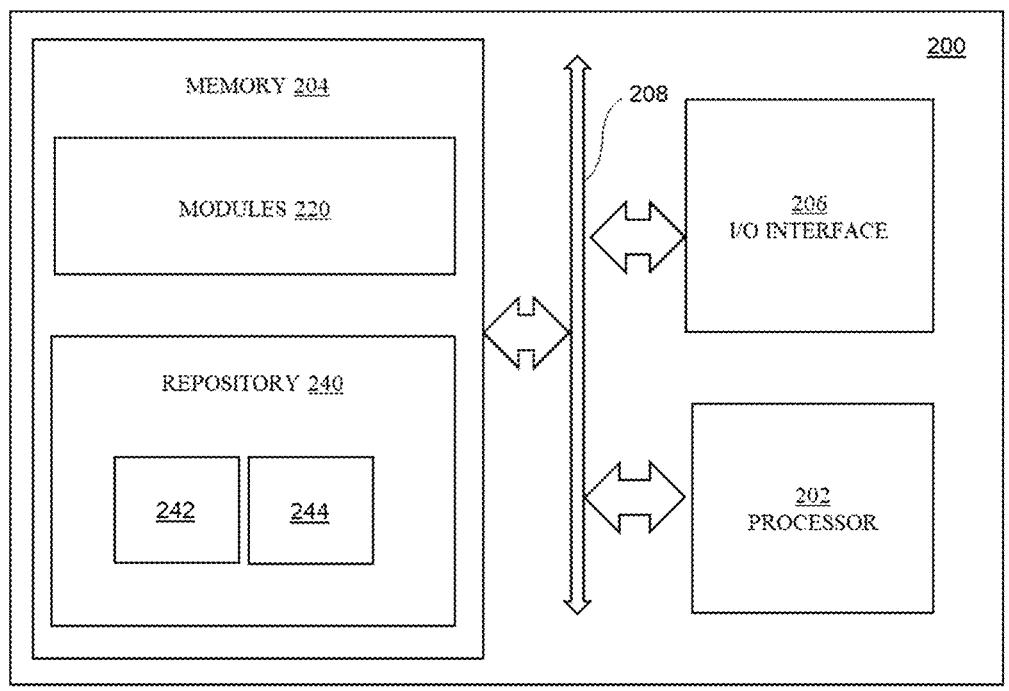
FIG. 2 illustrates a block diagram of a system for estimating quality of a food item contained in an enclosed package (of FIG. 1) is illustrated, according to some embodiments of the present disclosure.

Referring now to FIG. 2, a block diagram of a system for estimating quality of a food item contained in an enclosed package (for example, the enclosed package 100 of FIG. 1) is illustrated, according to some embodiments of the present disclosure. The system is capable of training a model for estimating the quality of food item based on a determination of value of electrical voltage and impedance of the food item in the enclosed package 100.

The system 200 includes or is otherwise in communication with one or more hardware processors such as a processor 202, at least one memory such as a memory 204, and an I/O interface 206. The processor 202, memory 204, and the I/O interface 206 may be coupled by a system bus such as a system bus 208 or a similar mechanism. The I/O interface 206 may include a variety of software and hardware interfaces, for example, a web interface, a graphical user interface, and the like. The interfaces 206 may include a variety of software and hardware interfaces, for example, interfaces for peripheral device(s), such as a keyboard, a mouse, an external memory, a camera device, and a printer. Further, the interfaces 206 may enable the system 200 to communicate with other devices, such as web servers and external databases. The interfaces 206 can facilitate multiple communications within a wide variety of networks and protocol types, including wired networks, for example, local area network (LAN), cable, etc., and wireless networks, such as Wireless LAN (WLAN), cellular, or satellite. For the purpose, the interfaces 206 may include one or more ports for connecting a number of computing systems with one another or to another server computer. The I/O interface 206 may include one or more ports for connecting a number of devices to one another or to another server.

The hardware processor 202 may be implemented as one or more microprocessors, microcomputers, microcontrollers, digital signal processors, central processing units, state machines, logic circuitries, and/or any devices that manipulate signals based on operational instructions. Among other capabilities, the hardware processor 202 is configured to fetch and execute computer-readable instructions stored in the memory 204.

The memory 204 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, the memory 204 includes a plurality of modules 220 and a repository 240 for storing data processed, received, and generated by one or more of the modules 220. The modules 220 may include routines, programs, objects, components, data structures, and so on, which perform particular tasks or implement particular abstract data types.

The repository 240, amongst other things, includes a system database 242 and other data 244. The other data 244 may include data generated as a result of the execution of one or more modules in the other modules 220. In an embodiment, the repository 240 may store a voltage spectrum and an impedance spectrum associated with the food item that may be indicative of quality of the food item. The voltage spectrum and the impedance spectrum may be obtained by changing the frequency over a range of AC (alternating current) to characterize the food item and correlate with quality over a period of time. In an embodiment, the voltage spectrum and the impedance spectrum may be utilized for training a food quality prediction algorithm to predict quality of various types of the food items. A method of quality estimation of a food item contained in the enclosed package (for example, the enclosed package 100) by using the system (for example, the system 200) is described further with reference to FIG. 3.

Figure 3:
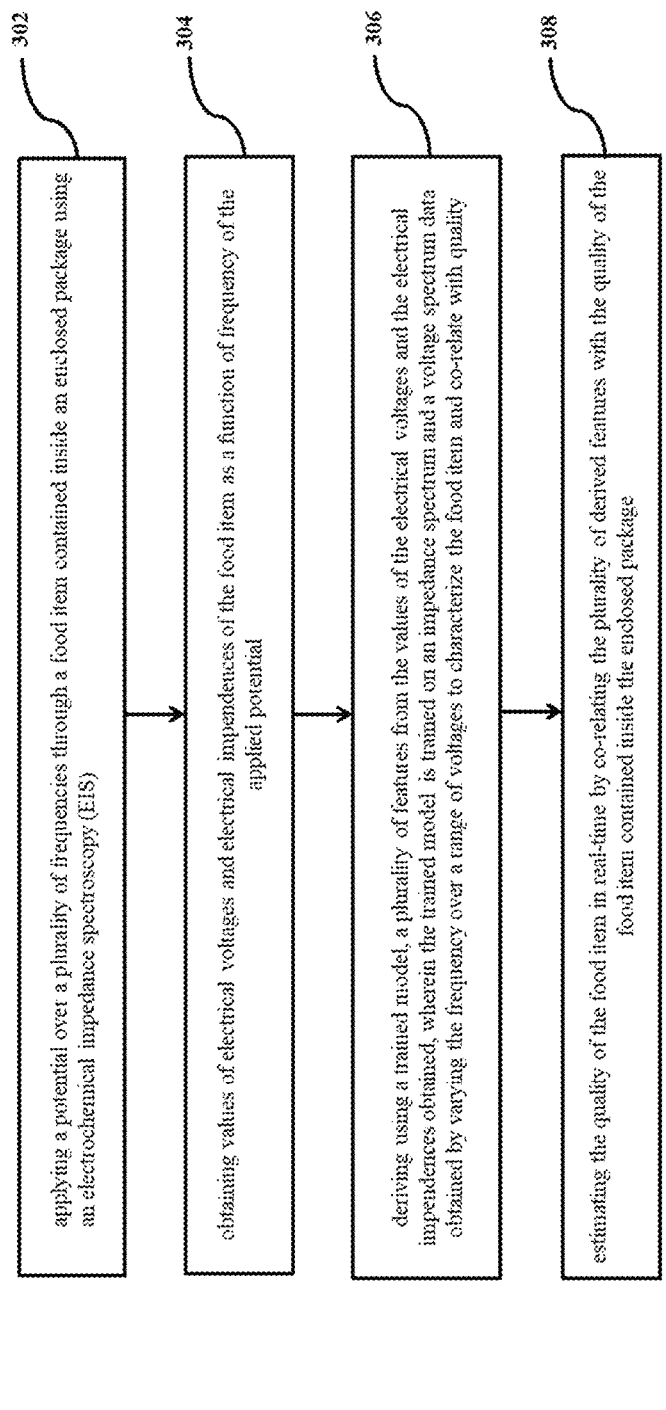
FIG. 3 illustrates a method for estimating quality of a food item contained in an enclosed package in accordance with some embodiments of the present disclosure.

Referring to FIG. 3, a flow diagram of a method 300 for quality estimation of a food item contained in the enclosed package is described in accordance with an example embodiment. The method 300 depicted in the flow chart may be executed by a system, for example, the system, 200 of FIG. 2. In an example embodiment, the system 200 may be embodied in a computing device. In another embodiment, the system 200 may be embodied in a potentiostat, as will be described further in the description.

Operations of the flowchart, and combinations of operation in the flowchart, may be implemented by various means, such as hardware, firmware, processor, circuitry and/or other device associated with execution of software including one or more computer program instructions. For example, one or more of the procedures described in various embodiments may be embodied by computer program instructions. In an example embodiment, the computer program instructions, which embody the procedures, described in various embodiments may be stored by at least one memory device of a system and executed by at least one processor in the system. Any such computer program instructions may be loaded onto a computer or other programmable system (for example, hardware) to produce a machine, such that the resulting computer or other programmable system embody means for implementing the operations specified in the flowchart. It will be noted herein that the operations of the method 300 are described with help of system 200. However, the operations of the method 300 can be described and/or practiced by using any other system.

Figure 4:
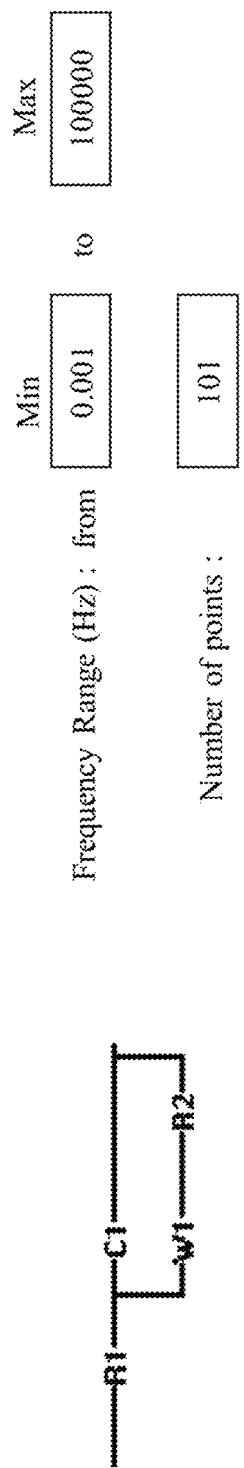
FIG. 4 illustrates an equivalent circuit of the food item in conjunction with a plurality of embedded electrodes using electrochemical impedance spectroscopy (EIS) by sweeping the frequency over a range of voltages in accordance with some embodiments of the present disclosure.

At step 302 of the method 300, the one or more hardware processors 202 apply a potential over a plurality of frequencies through a food item contained inside an enclosed package using electrochemical impedance spectroscopy (EIS). The potential is determined by using functionalized micro electrodes in at least one functional layer of a plurality of layers of the enclosed package, as described previously with reference to FIG. 1. Herein the word "potential" refers to the "voltage" and can be interchangeably used. In an example embodiment of the present disclosure, the potential or the voltage value of 100 mV with an AC (alternating current) amplitude of 10 mV and the frequency sweep or range of 0.001 Hz to 100 kHz with 101 sample points is applied through the food item (for example: apple juice) as depicted in FIG. 4. In an embodiment of the present disclosure, the plurality of frequencies or a range of frequencies of the potential or the voltage applied through the food item is specific to the biomarker present in the food item. For example., the potential with the plurality of frequencies which ranges from 0.001 to 100000 Hz is applied through the apple juice to determine the concentration of patulin, which serves as the biomarker for the estimation of the quality of apple juice. Herein, the terms "plurality of frequencies" and "range of frequencies" can be interchangeably used. It is to be understood by a person having ordinary skill in the art or a person skilled in the art that the above uses case or example shall not be construed as limiting the scope of the present disclosure.

At step 304 of the method 300, the one or more hardware processors 202 obtain values of electrical voltages and electrical impedances of the food item as a function of frequency of the applied potential. At step 306 of the method 300, the one or more hardware processors 202 derive using a trained model, a plurality of features from the values of the electrical voltages and the electrical impedances obtained, wherein the trained model is trained on an impedance spectrum and a voltage spectrum data obtained by varying the frequency over a range of voltages to characterize the food item and correlate with quality.

As described with reference to FIG. 2, the trained model may be trained on an impedance spectrum and a voltage spectrum obtained by changing the frequency over a range of AC (alternating current) as depicted in FIG. 4 to characterize the food item and correlate with quality. In an alternate embodiment, the impedance spectrum and the voltage spectrum may be utilized for training a prediction model capable of predicting the quality of various food items in real-time. In yet another embodiment, the trained model may facilitate development of a portable potentiostat to access the microelectrodes externally and non-invasively and estimate the quality of the food items on the basis of the response curves e.g., Nyquist plots correlated with quality of the food item such as juice, milk etc. as depicted from FIGS. 5A through 5F. The Nyquist plots facilitate in deriving features which can be correlated to the degradation of the food item via an AI (Artificial Intelligence) based model. For example, the AI (Artificial Intelligence) based data driven model may take Nyquist and Bode plots and features extracted in correlation with food quality as inputs. In an embodiment, the method embodied in a set of software instructions to estimate quality of a specific food item e.g., Apple juice vs. the resulting Nyquist plot may be embodied in the potentiostat. Further, training the model includes modelling the spoilage of the food item (for e.g., apple juice) using different paradigms for machine learning feature extractions e.g., Autoencoders.

At step 308 of the method 300, the one or more hardware processors 202 estimate the quality of the food item in real-time by co-relating the plurality of derived features with the quality of the food item contained inside the enclosed package.

FIG. 4 illustrates an equivalent circuit of the food item (for e.g., apple juice) in conjunction with a plurality of embedded electrodes using electrochemical impedance spectroscopy by sweeping the frequency over a range of voltages in accordance with some embodiments of the present disclosure. Referring to FIG. 4, R1 represents a solution resistant, C1 represents a double layer capacitance, W1 represents a Warburg impedance, R2 represents a charge transfer resistance.

Figure 5A:
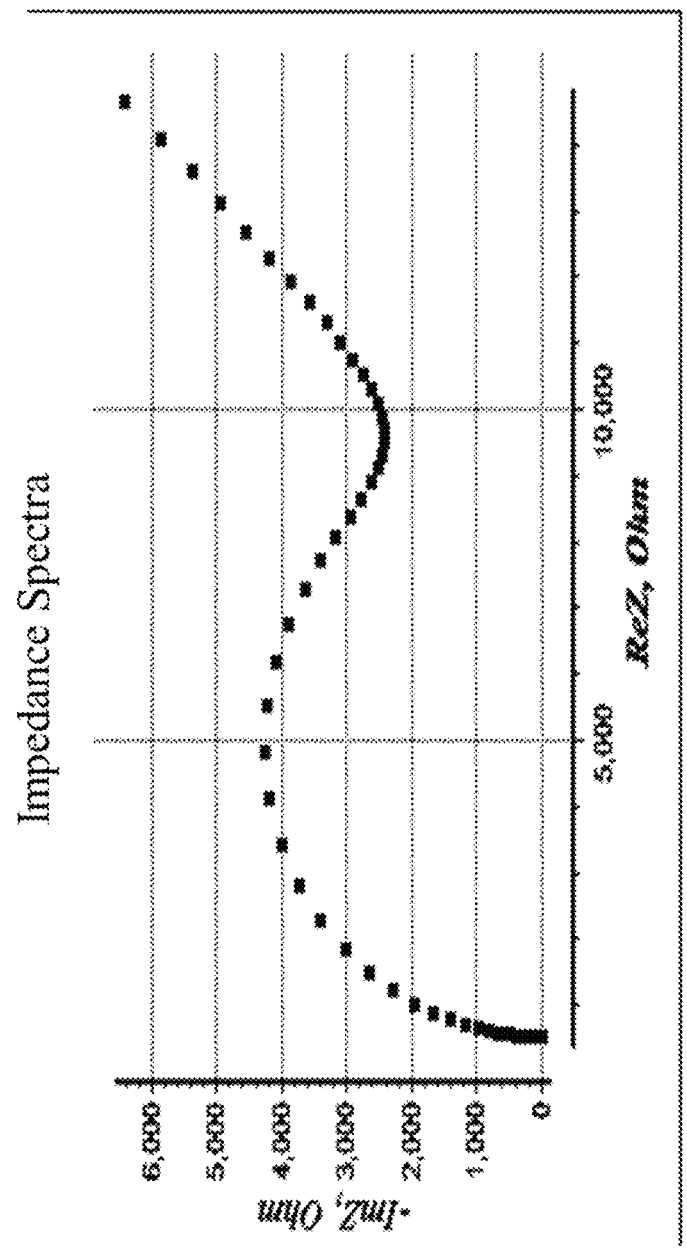
FIGS. 5A through 5F shows a use case example for the simulated results illustrating the effect of change in a Patulin concentration in an apple juice contained in an enclosed package, on a Nyquist plot in accordance with some embodiments of the present disclosure.
Figure 5B:
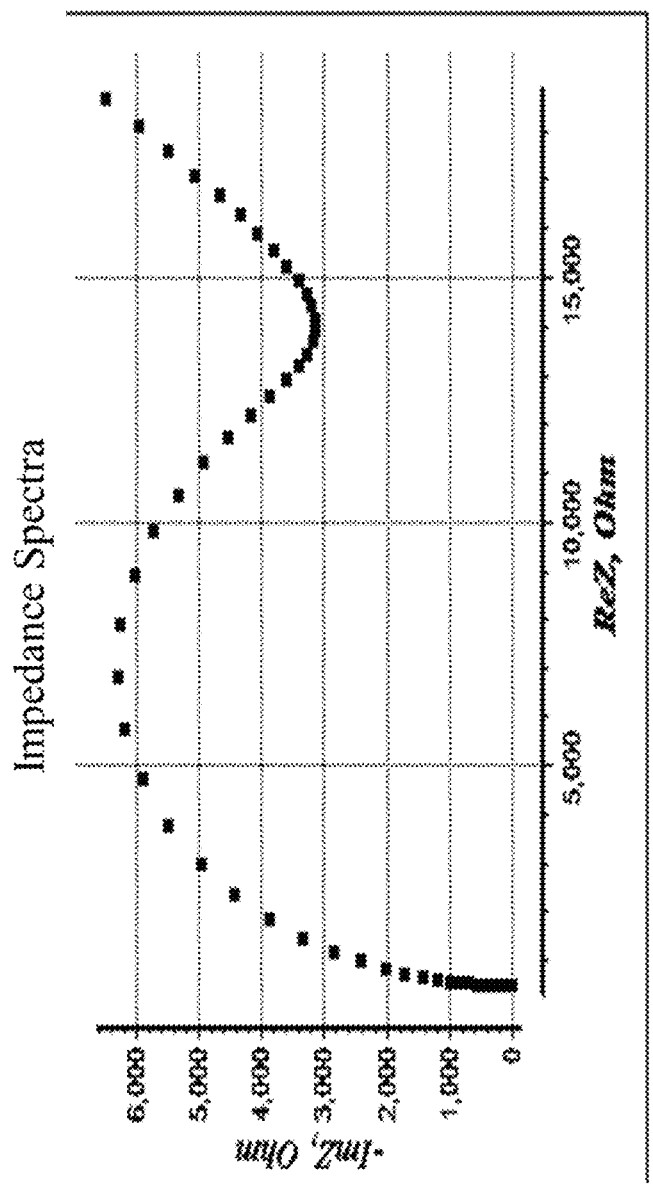
Figure 5C:
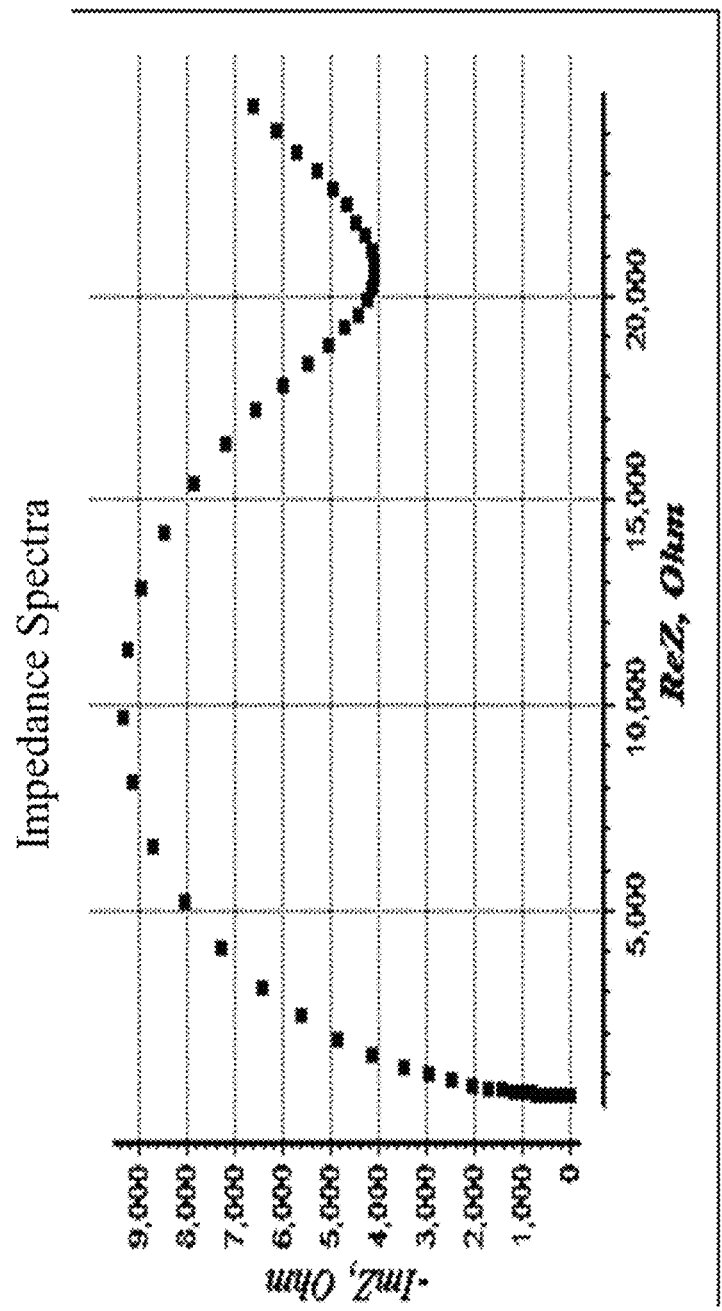
Figure 5D:
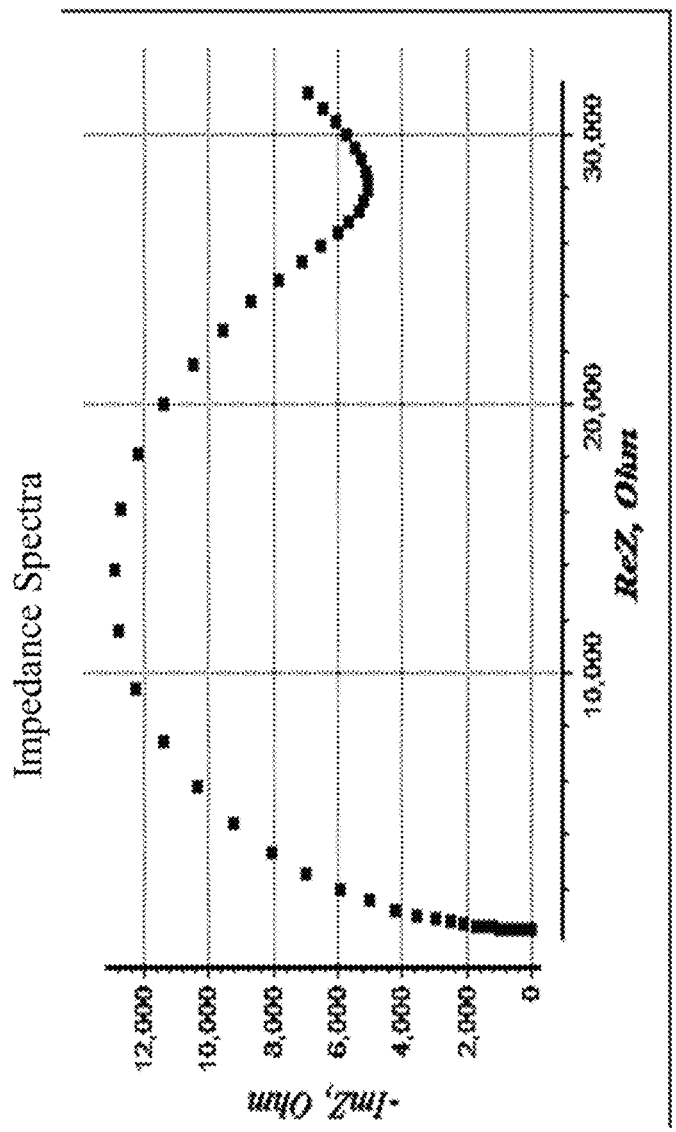
Figure 5E:
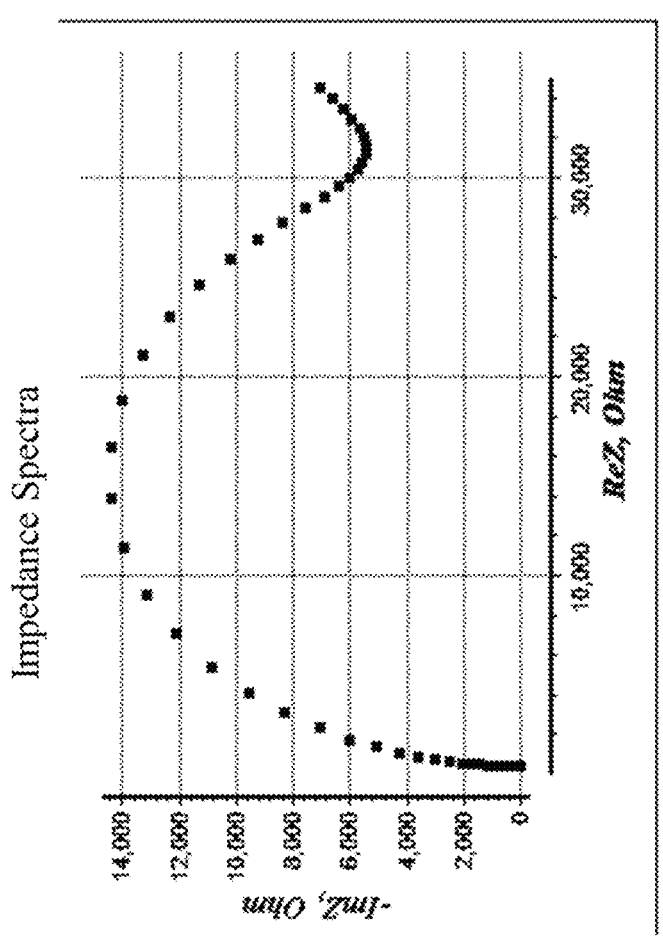
Figure 5F:
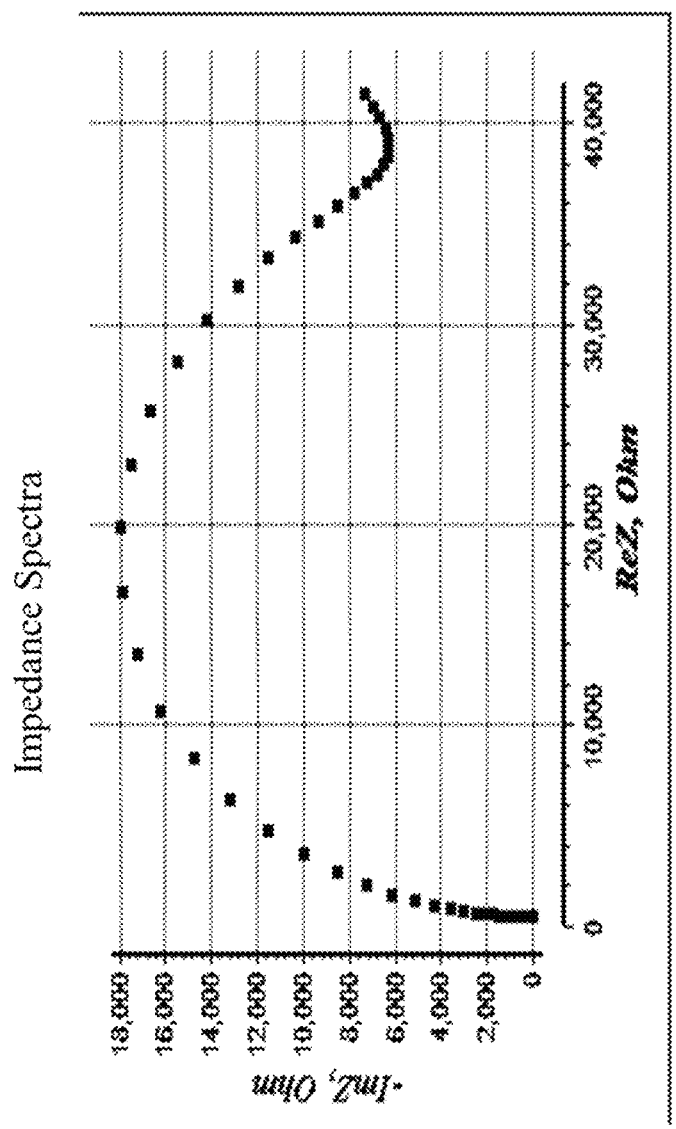

FIGS. 5A through 5F shows a use case example for the simulated results illustrating the effect of change in a Patulin concentration in an apple juice contained in the enclosed package, on a Nyquist plot in accordance with some embodiments of the present disclosure. Fruit juice usually contain sugars, organic acids, vitamins, phenolic compounds, and the like. The concentration of the chemical compounds present in the fruit juice usually undergo changes when spoilage occurs in the fruit juice. In an example embodiment, consider an apple juice which is a mixture of sugars (primarily fructose, glucose, and sucrose), oligosaccharides, and polysaccharides (e.g., starch) together with malic, quinic, citro malic acids, tannins (i.e., polyphenols), amides, other nitrogenous compounds, soluble pectin, vitamin C, minerals, and a diverse range of esters that give the apple juice a typical apple-like aroma (e.g., ethyl- and methyl-iso-valerate). Patulin is a mycotoxin usually present in apple juices and the concentration of patulin in the apple juice serves as an indicator of the quality of the apple juice. In an embodiment of the present disclosure, electrochemical impedance spectroscopy (EIS) is the technique used to determine the concentration of patulin in the apple juice. The possible equivalent circuit of the apple juice in conjunction with the electrodes is illustrated in FIG. 4. As the Patulin concentration rises, the quality of the apple juice degrades. Further, the degradation of the apple juice is observed as an increase in the charge transfer resistance in the Nyquist plots as depicted in the FIGS. 5A through 5F. Referring to the FIGS. 5A through 5F, the simulated results illustrating the effect of the change in the Patulin concentration contained in the apple juice is presented in the subsequent curves on the Nyquist plot. FIG. 5A depicts the change in the Patulin concentration contained in the apple juice for the parameter values $R_1=500$, $C_1=100$, $R_2=8000$, $Z_W=500$. FIG. 5B depicts the change in the Patulin concentration contained in the apple juice for the parameter values $R_1=500$, $C_1=100$, $R_2=12000$, $Z_W=500$. FIG. 5C depicts the change in the Patulin concentration contained in the apple juice for the parameter values $R_1=500$, $C=100$, $R_2=18000$, $Z_W=500$. FIG. 5D depicts the change in the Patulin concentration contained in the apple juice for the parameter values $R_1=500$, $C_1=100$, $R_2=25000$, $Z_W=500$. FIG. 5E depicts the change in the Patulin concentration contained in the apple juice for the parameter values $R_1=500$, $C_1=100$, $R_2=28000$, $Z_W=500$. FIG. 5F depicts the change in the Patulin concentration contained in the apple juice for the parameter values $R_1=500$, $C_1=100$, $R_2=35000$, $Z_W=500$. In an embodiment of the present disclosure, the biomarker present in the food item serves as an indicator for the estimation of the quality of the food item contained in the enclosed package. It should be noted that, as the concentration of the Paulin contained in the apple juice increases the quality of the apple juice degrades which is reflected by the value R2 which represents the charge transfer resistance as depicted in FIGS. 5A through 5F. The above-mentioned procedure can be implemented for other biomarkers (for e.g., glucose, lactic acid, etc.,) as well. In an embodiment of the present disclosure, the biomarker present in the food item serves as an indicator for the estimation of the quality of the food item contained in the enclosed package. It should be noted that the maximum admissible limit of Patulin concentration is 50 µg L-1 or 50 ppb, as defined by European Union (EU), United States Food and Drug Administration (FDA) and Food Safety and Standards Authority of India (FSSAI). In another example embodiment, consider grape juice which contains Lactic Acid Bacteria produces lactic acid by metabolizing sugars. Here the lactic acid concentration in the grape juice is used to predict the quality or degradation of the grape juice. In the similar way, when milk spoilage occurs the pH falls, and the lactic acid concentration increases, wherein the lactic acid concentration may be determined using electrochemical impedance spectroscopy (EIS). It is to be understood by a person having ordinary skill in the art or a person skilled in the art that the above uses cases or examples shall not be construed as limiting the scope of the present disclosure.

Figure 6:
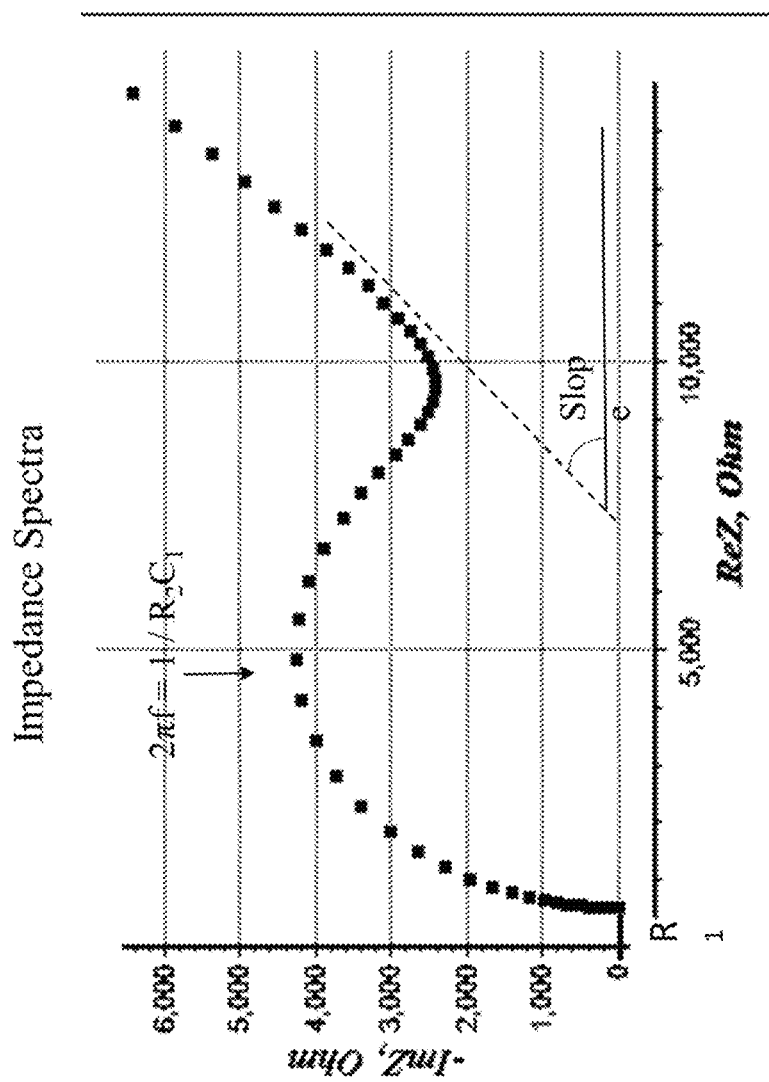
FIG. 6 shows a use case example illustrating a plurality of features derived from the Nyquist plot in accordance with some embodiments of the present disclosure.

FIG. 6 shows a use case example illustrating a plurality of features derived from the Nyquist plot in accordance with some embodiments of the present disclosure. The plurality of features derived from the Nyquist plots may include a slope of the straight line, peak of the semi-circle R1, the frequency where the peak occurs, diameter of the semi-circle and the like as depicted in FIG. 6.

Figure 7:
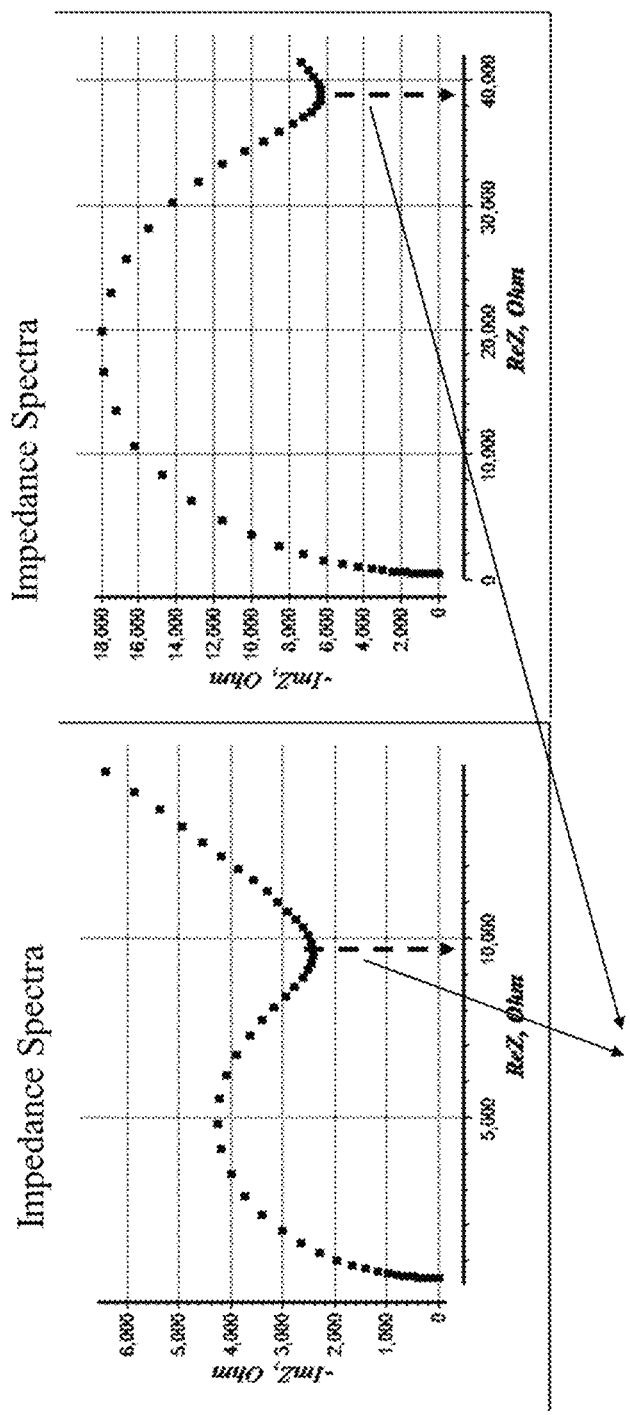
FIG. 7 shows a use case example illustrating the implementation of Nyquist Plot features to differentiate between two samples of the food item which differ in quality in accordance with some embodiments of the present disclosure.

FIG. 7 shows a use case example illustrating the implementation of Nyquist Plot features to differentiate between two samples of the food item which differ in quality in accordance with some embodiments of the present disclosure. In an example embodiment, consider a Tetra Pak containing the food item (for e.g., apple juice) wherein the tetra Pak includes the microelectrodes etched on the Aluminium layer of the Tetra Pak. The Potentiostat or a circuit mimicking its behavior scans the Tetra Pak and generates the Nyquist plots. The different diameter of the Nyquist plot indicates varying concentrations of the biomarker or the quality indicator of the food item (for e.g., apple juice) contained inside the Tetra Pak. It should be noted that the different diameters of the Nyquist plot represent the features which differentiate between two samples of the food item (for e.g., apple juice) obtained at different instances as depicted in FIG. 7. Once the spoilage or degradation of the food item or the quality of the food item contained inside the Tetra Pak is estimated using the trained model, the results are displayed by a display panel comprised in the Potentiostat. In another embodiment, a mobile application running the trained models in the background, scans the Nyquist plot and provides insights about the quality of the food item contained inside the Tetra Pak.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

Various embodiments disclosed herein provide method and system for estimating quality of food items contained in a packaged container. The embodiments of present disclosure herein address unresolved problem of non-invasively determining the quality of packaged food items in real time.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g., any kind of computer like a server or a personal computer, or the like, or any combination thereof. The device may also include means which could be e.g., hardware means like e.g., an application-specific integrated circuit (ASIC), a field-programmable gate array (FPGA), or a combination of hardware and software means, e.g., an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g., using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor-implemented method for real-time non-invasive estimation of food quality within an enclosed package, the method comprising:
   applying, via one or more hardware processors, a predefined potential with an alternating predefined current amplitude from an AC source over a plurality of frequencies with a predefined sweep through a food item contained inside the enclosed package, wherein the plurality of frequencies of the potential applied through the food item is specific to a biomarker present in the food item;
   obtaining, via the one or more hardware processors, values of electrical voltages and electrical impedances of the food item as a function of frequency of the applied potential through an equivalent circuit comprising a resistance R1 representing a solution resistant, a capacitance C1 representing a double layer capacitance, an impedance W1 representing a Warburg impedance, resistance R2 representing a charge transfer resistance of the food item in conjunction with a plurality of micro-electrodes etched on an Aluminium layer of a packaging material of the food item, using electrochemical impedance spectroscopy by sweeping the frequency over a range of potentials, wherein the electrochemical impedance spectroscopy is a technique used to determine a change in concentration of plurality of chemical compounds present in the food item;

deriving, using a trained model capable of predicting quality of food items in real-time via the one or more hardware processors, a plurality of features from the values of the electrical voltages and the electrical impedances obtained, wherein the trained model is trained on an impedance spectrum and a voltage spectrum data obtained by varying the frequency over a range of voltages to characterize the food item and correlate with quality, wherein the biomarker present in the food item serves as an indicator for the estimation of quality of the food item contained in the enclosed package; and estimating, via the one or more hardware processors, the quality of the food item in real-time by co-relating the plurality of derived features with the quality of the food item contained inside the enclosed package.

2. The method of claim 1, wherein the enclosed package comprises of a plurality of layers which includes a plurality of polyethylene layers and a conducting layer arranged between two adjacent polyethylene layers.

3. The method of claim 2, wherein the conducting layer comprised in the enclosed package further comprises of functionalized micro-electrodes for specific quality indicators associated with the food item contained in the enclosed package and area configured therein to determine the variation in applied potential over the plurality of frequencies associated with the food item, wherein the functionalized micro-electrodes are created between the conducting layer and the food item, when the food item comes in contact with the micro-electrodes etched on an Aluminium layer of the packaging material.

4. A system for real-time non-invasive estimation of food quality within an enclosed package, comprising:
  a memory storing instructions;
  one or more communication interfaces; and
  one or more hardware processors coupled to the memory via the one or more communication interfaces, wherein the one or more hardware processors are configured by the instructions to:
  apply, a pre-defined potential with an alternating pre-defined current amplitude from an AC source over a plurality of frequencies with a predefined sweep through a food item contained inside the enclosed package, wherein the plurality of frequencies of the potential applied through the food item is specific to a biomarker present in the food item;
  obtain, values of electrical voltages and electrical impedances of the food item as a function of frequency of the applied potential through an equivalent circuit comprising a resistance R1 representing a solution resistant, a capacitance C1 representing a double layer capacitance, an impedance W1 representing a Warburg impedance, resistance R2 representing a charge transfer resistance of the food item in conjunction with a plurality of micro-electrodes etched on an aluminium layer of a packaging material of the food item, using electrochemical impedance spectroscopy by sweeping the frequency over a range of potentials, wherein the electrochemical impedance spectroscopy is a technique used to determine a change in concentrating of plurality of chemical compounds present in the food item;
  derive, using a trained model capable of predicting quality of food items in real-time, a plurality of features from the values of the electrical voltages and the electrical impedances obtained, wherein the trained model is trained on an impedance spectrum and a voltage spectrum data obtained by varying the frequency over a range of voltages to characterize the food item and correlate with quality, wherein the biomarker present in the food item serves as an indicator for the estimation of quality of the food item contained in the enclosed package; and
  estimate, the quality of the food item in real-time by co-relating the plurality of derived features with the quality of the food item contained inside the enclosed package.

5. The system of claim 4, wherein the enclosed package comprises of a plurality of layers which includes a plurality of polyethylene layers and a conducting layer arranged between two adjacent polyethylene layers.

6. The system of claim 5, wherein the conducting layer comprised in the enclosed package further comprises of functionalized micro-electrodes for specific quality indicators associated with the respective food item contained in the enclosed package and are configured therein to determine the variation in applied potential over the plurality of frequencies associated with the food item, wherein the functionalized micro-electrodes are created between the conducting layer and the food item, when the food item comes in contact with the micro-electrodes etched on an Aluminium layer of the packaging material.

7. One or more non-transitory machine-readable information storage mediums for real-time non-invasive estimation of food quality within an enclosed package, comprising one or more instructions which when executed by one or more hardware processors cause:
  applying, a predefined potential with an alternating pre-defined current amplitude from an AC source over a plurality of frequencies with a predefined sweep through a food item contained inside the enclosed package, wherein the plurality of frequencies of the potential applied through the food item is specific to a biomarker present in the food item;
  obtaining, values of electrical voltages and electrical impedances of the food item as a function of frequency of the applied potential through an equivalent circuit comprising a resistance R1 representing a solution resistant, a capacitance C1 representing a double layer capacitance, an impedance W1 representing a Warburg impedance, resistance R2 representing a charge transfer resistance of the food item in conjunction with a plurality of micro-electrodes etched on an Aluminium layer of a packaging material of the food item, using electrochemical impedance spectroscopy by sweeping the frequency over a range of potentials, wherein the electrochemical impedance spectroscopy is a technique used to determine a change in concentration of plurality of chemical compounds present in the food item;
  deriving, using a trained model capable of predicting quality of food items in real-time, a plurality of features from the values of the electrical voltages and the electrical impedances obtained, wherein the trained model is trained on an impedance spectrum and a voltage spectrum data obtained by varying the frequency over a range of voltages to characterize the food item and correlate with quality, wherein the biomarker present in the food item serves as an indicator for the estimation of quality of the food item contained in the enclosed package; and estimating, the quality of the food item in real-time by co-relating the plurality of derived features with the quality of the food item contained inside the enclosed package.

8. The one or more non-transitory machine readable information storage mediums of claim 7, wherein the enclosed package comprises of a plurality of layers which includes a plurality of polyethylene layers and a conducting layer arranged between two adjacent polyethylene layers.

9. The one or more non-transitory machine readable information storage mediums of claim 8, wherein the conducting layer comprised in the enclosed package further comprises of functionalized micro-electrodes for specific quality indicators associated with the food item contained in the enclosed package and area configured therein to determine the variation in applied potential over the plurality of frequencies associated with the food item, wherein the functionalized micro-electrodes are created between the conducting layer and the food item, when the food item comes in contact with the micro-electrodes etched on an Aluminium layer of the packaging material.

* * * * *